(12) United States Patent
Hug et al.

(10) Patent No.: US 10,292,917 B2
(45) Date of Patent: May 21, 2019

(54) ORAL CARE COMPOSITION

(71) Applicant: GABA International Holding AG, Therwil (CH)

(72) Inventors: Angelique Hug, Rixheim (FR); Tilo Poth, Weinheim (DE); René Heckendorn, Basel (CH)

(73) Assignee: Colgate-Palmolive Company, New York, NY (US)

( * ) Notice: Subject to any disclaimer, the term of this patent is extended or adjusted under 35 U.S.C. 154(b) by 45 days.

(21) Appl. No.: 14/654,515

(22) PCT Filed: Dec. 21, 2012

(86) PCT No.: PCT/EP2012/076776
§ 371 (c)(1),
(2) Date: Jun. 20, 2015

(87) PCT Pub. No.: WO2014/094900
PCT Pub. Date: Jun. 26, 2014

(65) Prior Publication Data
US 2015/0366768 A1 Dec. 24, 2015

(51) Int. Cl.
| | | |
|---|---|---|
| *A61K 8/00* | (2006.01) | |
| *A61K 8/14* | (2006.01) | |
| *A61K 8/41* | (2006.01) | |
| *A61Q 11/00* | (2006.01) | |
| *A61K 8/69* | (2006.01) | |
| *A61K 8/81* | (2006.01) | |
| *A61K 8/19* | (2006.01) | |

(52) U.S. Cl.
CPC .............. *A61K 8/41* (2013.01); *A61K 8/19* (2013.01); *A61K 8/69* (2013.01); *A61K 8/8164* (2013.01); *A61Q 11/00* (2013.01); *A61K 2800/95* (2013.01)

(58) Field of Classification Search
CPC ... A61K 8/00; A61K 8/19; A61K 8/21; A61K 8/41; A61K 8/69; A61K 8/8164; A61Q 11/00
See application file for complete search history.

(56) References Cited

U.S. PATENT DOCUMENTS

| | | |
|---|---|---|
| 4,521,551 A | 6/1985 | Chang et al. |
| 5,017,363 A | 5/1991 | Suhonen |
| 5,395,241 A | 3/1995 | Kandelman |
| 5,616,316 A | 4/1997 | Persello |
| 6,583,225 B1 | 6/2003 | Plochocka et al. |
| 6,706,817 B2 | 3/2004 | Plochocka et al. |
| 8,974,772 B2 | 3/2015 | Fruge et al. |
| 2001/0006622 A1* | 7/2001 | Heckendorn ............ A61K 8/69 424/49 |
| 2003/0236349 A1 | 12/2003 | Plochocka et al. |
| 2004/0126335 A1* | 7/2004 | Faller ...................... A23G 4/06 424/52 |
| 2006/0140885 A1 | 6/2006 | Gaffar et al. |
| 2007/0025928 A1 | 2/2007 | Glandorf et al. |
| 2009/0042161 A1 | 2/2009 | Jodaikin et al. |
| 2009/0202456 A1 | 8/2009 | Prencipe et al. |
| 2009/0311200 A1 | 12/2009 | Lambert et al. |
| 2010/0316580 A1 | 12/2010 | Kohli et al. |
| 2012/0034280 A1* | 2/2012 | Cohen ..................... A61K 8/20 424/401 |
| 2012/0100193 A1 | 4/2012 | Nowak et al. |
| 2014/0370292 A1 | 12/2014 | Ceresa et al. |

FOREIGN PATENT DOCUMENTS

| | | |
|---|---|---|
| EP | 0549281 | 4/1999 |
| WO | WO 08/041055 | 4/2008 |
| WO | WO 10/037701 | 4/2010 |

OTHER PUBLICATIONS

Loveren, "Toothpastes", Karger Medical and Scientific Publishers, Jun. 19, 2013, p. 6.*
Commercially available product Elmex Sensitive Plus toothpaste with amine fluoride, 2009.
Embleton et al., 1998, "Influence of Grown Mode and Sucrose on Susceptibility of *Streptococcus sanguis* to Amine Fluorides and Amine Fluoride-Inorganic Fluoride Combinations," Applied and Environmental Microbiology 64(9):3503-3506.
GABA International, 2001, "Amine Fluorides," website URL: http://www.gaba.com/en/417/Amine-fluorides.htm?Subnav2=AmineFluoride&Article=16850.
Ganss et al., 2004, "Effects of two fluoridation measures on erosion progression in human enamel and denine in situ," Caries Research 38(6):561-566.
Holler et al., 2002, "Fluoride uptake and distribution in enamel and dentin after application of different fluoride solutions," Clin. Oral Investigation 6:137-144.
International Search Report and Written Opinion in International Application No. PCT/EP2012/076776, dated Sep. 30, 2013.
Written Opinion in International Application No. PCT/EP2012/076776, dated Dec. 23, 2014.

* cited by examiner

*Primary Examiner* — Lezah Roberts

(57) ABSTRACT

An oral care composition is provided. The composition comprises (a) a first component comprising an amine fluoride; and (b) a second component comprising an acidic polymer; wherein the amine fluoride and acidic polymer have respective first and second reactive groups which are arranged to react together to form a cross-linked copolymer of the amine fluoride and acidic polymer when the composition is applied to an oral cavity.

29 Claims, No Drawings

ORAL CARE COMPOSITION

BACKGROUND OF THE INVENTION

The amine fluoride Olaflur (N,N,N'-tris(2-hydroxyethyl)-N'-octadecylpropane-1,3-diamine dihydrofluoride) is known as an agent for protecting the teeth against the formation of dental caries. Olaflur is believed to form a layer on the surface of the teeth, allowing for incorporation of fluoride into the tooth enamel. Such a layer is also believed to provide some protection against acid attack.

However, it is believed that this layer of the water-soluble amine fluoride is diluted and removed from the teeth by attacking acid after a relatively short period of time.

There is therefore a need in the art to provide compositions which can provide increased protection against acid attack, and which are effective for a longer time period.

BRIEF SUMMARY OF THE INVENTION

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

A first aspect of the present invention provides an oral care composition comprising: (a) a first component comprising an amine fluoride; and (b) a second component comprising an acidic polymer; wherein the amine fluoride and acidic polymer have respective first and second reactive groups which are arranged to react together to form a cross-linked copolymer of the amine fluoride and acidic polymer when the composition is applied to an oral cavity.

Optionally, the amine fluoride comprises hydroxyalkyl groups as the first reactive groups. Optionally, the hydroxyalkyl groups are hydroxyethyl groups.

Optionally, the amine fluoride comprises at least one $C_{10}$ to $C_{24}$ carbon chain. Optionally, the carbon chain has an even-numbered chain length. Optionally, the carbon chain is decyl, dodecyl (lauryl), tetradecyl (myristyl), hexadecyl (cetyl, palmityl), octadecyl (stearyl), eicosanyl, 9-cis-octadecen-1-yl (oleyl), 9-trans-octadecen-1-yl (elaidyl), cis,cis-9,12-octadecadien-1-yl (linolyl), cis,cis,cis-9,12,15-octadecatrien-1-yl (linolenyl) or 9-cis-eicosaen-1-yl (gadolyl). Optionally, the carbon chain is a $C_{18}$ carbon chain.

Optionally, the amine fluoride comprises at least one of N,N,N'-tris(2-hydroxyethyl)-N'-octadecylpropane-1,3-diamine dihydrofluoride; N,N-bis(2-hydroxyethyl)oleylamine hydrofluoride; and N,N-bis(2-hydroxyethyl)octadecylamine hydrofluoride. N,N,N'-tris(2-hydroxyethyl)-N'-octadecylpropane-1,3-diamine dihydrofluoride is identified as "Olaflur" hereinafter. N,N-bis(2-hydroxyethyl)oleylamine hydrofluoride is identified as "Xidecaflur" hereinafter. N,N-bis(2-hydroxyethyl)octadecylamine hydrofluoride is identified as "Steraflur" hereinafter.

Optionally, the amine fluoride is Olaflur and the first component further comprises 9-octadeceylamine hydrofluoride. 9-octadeceylamine hydrofluoride will be identified as "Dectaflur" hereinafter. Optionally, the ratio of Olaflur to Dectaflur in the first component is from 20:1 to 1:1, optionally from 15:1 to 5:1, further optionally 10.6:1.

Optionally, the acidic polymer comprises carboxylic acid groups as the second reactive groups.

Optionally, the acidic polymer comprises monomers of maleic acid or maleic anhydride. Optionally, the acidic polymer is a copolymer of maleic acid or maleic anhydride with an alkylvinylether. Optionally, the alkylvinylether is methylvinylether.

Optionally, the acidic polymer comprises acrylic acid monomers. Optionally, the acidic polymer is polyacrylic acid.

Optionally, the amine fluoride is present in a concentration of 0.1 wt % to 22 wt %, based on the total weight of the oral care composition; optionally 1 wt % to 12 wt %, based on the total weight of the oral care composition; optionally 6 wt % to 10 wt %, based on the total weight of the oral care composition.

Optionally, the acidic polymer is present in a concentration of 0.1 wt % to 30 wt %, based on the total weight of the oral care composition; optionally 1 wt % to 15 wt %, based on the total weight of the oral care composition; optionally 5 wt % to 12 wt %, based on the total weight of the oral care composition.

Optionally, the concentration ratio of the amine fluoride to the acidic polymer in the oral care composition is from 1:1000 to 1:1; optionally from 1:100 to 1:2; optionally from 1:20 to 1:3.

Optionally, the oral care composition further comprises stannic oxide, $SnO_2$. Preferably, the stannic oxide is nanoparticulate stannic oxide.

Optionally, the stannic oxide is present in the oral care composition in a concentration of 0.1 wt % to 3 wt %, based on the total weight of the oral care composition; optionally 0.3 wt % to 2 wt %, based on the total weight of the oral care composition; optionally 0.5 wt % to 1 wt %, based on the total weight of the oral care composition.

Optionally, the amine fluoride and the acidic polymer are maintained separately from one another in the oral care composition.

Optionally, the first component is a first oral care composition and the second component is a second oral care composition, the first and second oral care compositions being maintained separately from one another. Optionally, the second composition is a mouthwash or a tooth gel.

Optionally, the amine fluoride is present in the first oral care composition in a concentration of 0.1 to 20 wt % based on the weight of the first oral care composition; optionally 1 to 15 wt % based on the weight of the first oral care composition; optionally 5 to 12 wt % based on the weight of the first oral care composition; optionally 9 wt % based on the weight of the first oral care composition.

Optionally, the acidic polymer is present in the second oral care composition in a concentration of 0.1 wt % to 30 wt %, based on the weight of the second oral care composition; optionally 1 wt % to 15 wt %, based on the weight of the second oral care composition; optionally 5 wt % to 12 wt %, based on the weight of the second oral care composition.

Optionally, stannic oxide is present in the first composition. Alternatively, stannic oxide may be present in the second composition. Preferably, the stannic oxide is nanoparticulate stannic oxide.

A second aspect of the present invention provides a method of treating or preventing a disease or condition of the oral cavity, comprising applying an oral care composition of the present invention to the oral cavity.

Optionally, the disease or condition of the oral cavity is one or more of acid erosion, caries formation, demineralisation.

A third aspect of the present invention provides a method of protecting a tooth surface against acid attack, the method comprising applying an oral care composition of the present invention to a tooth surface.

A fourth aspect of the invention provides a method of treating or preventing a disease or condition of the oral cavity, comprising the steps of: (a) contacting an oral surface with an amine fluoride; and subsequently (b) contacting the oral surface with an acidic polymer; wherein the amine fluoride and acidic polymer have respective first and second reactive groups which are arranged to react together to form a cross-linked copolymer of the amine fluoride and acidic polymer on the oral surface.

Optionally, the disease or condition of the oral cavity is one or more of acid erosion, caries formation, demineralisation.

Optionally, the amine fluoride comprises hydroxyalkyl groups as the first reactive groups. Optionally, the hydroxyalkyl groups are hydroxyethyl groups.

Optionally, the amine fluoride comprises at least one $C_{10}$ to $C_{24}$ carbon chain. Optionally, the carbon chain has an even-numbered chain length. Optionally, the carbon chain is decyl, dodecyl (lauryl), tetradecyl (myristyl), hexadecyl (cetyl, palmityl), octadecyl (stearyl), eicosanyl, 9-cis-octadecen-1-yl (oleyl), 9-trans-octadecen-1-yl (elaidyl), cis,cis-9,12-octadecadien-1-yl (linolyl), cis,cis,cis-9,12,15-octadecatrien-1-yl (linolenyl) or 9-cis-eicosaen-1-yl (gadolyl). Optionally, the carbon chain is a $C_{18}$ carbon chain.

Optionally, the amine fluoride comprises at least one of Olaflur, Xidecaflur, and Steraflur.

Optionally, the amine fluoride is Olaflur and the oral surface is also contacted with Dectaflur in step a). Optionally, the ratio of Olaflur to Dectaflur is from 20:1 to 1:1, optionally from 15:1 to 5:1, further optionally 10.6:1.

Optionally, the acidic polymer comprises carboxylic acid groups as the second reactive groups.

Optionally, the acidic polymer comprises monomers of maleic acid or maleic anhydride. Optionally, the acidic polymer is a copolymer of maleic acid or maleic anhydride with an alkylvinylether. Optionally, the alkylvinylether is methylvinylether.

Optionally, the acidic polymer comprises acrylic acid monomers. Optionally, the acidic polymer is polyacrylic acid.

Optionally, the concentration ratio of the amine fluoride to the acidic polymer is from 1:1000 to 1:1; optionally from 1:100 to 1:2; optionally from 1:20 to 1:3.

Optionally, the oral surface is also contacted with stannic oxide, $SnO_2$. Preferably, the stannic oxide is nano-particulate stannic oxide.

Optionally, the amine fluoride and the acidic polymer are maintained separately from one another prior to contacting with the oral surface.

Optionally, the amine fluoride is present in a first oral care composition and the acidic polymer is present in a second oral care composition, the first and second oral care compositions being maintained separately from one another prior to contacting with the oral surface. Optionally, the second oral care composition is a mouthwash or a tooth gel.

Optionally, the amine fluoride is present in the first oral care composition in a concentration of 0.1 to 20 wt % based on the weight of the first oral care composition; optionally 1 to 15 wt % based on the weight of the first oral care composition; optionally 5 to 12 wt % based on the weight of the first oral care composition; optionally 9 wt % based on the weight of the first oral care composition.

Optionally, the acidic polymer is present in the second oral care composition in a concentration of 0.1 wt % to 30 wt %, based on the weight of the second oral care composition; optionally 1 wt % to 15 wt %, based on the weight of the second oral care composition; optionally 5 wt % to 12 wt %, based on the weight of the second oral care composition.

Optionally, stannic oxide is present in the first composition. Alternatively, stannic oxide may be present in the second composition. Preferably, the stannic oxide is nano-particulate stannic oxide.

A fifth aspect of the present invention provides a method of protecting a tooth surface against acid attack, comprising the steps of: (a) contacting the tooth surface with an amine fluoride; and subsequently (b) contacting the tooth surface with an acidic polymer; wherein the amine fluoride and acidic polymer have respective first and second reactive groups which are arranged to react together to form a cross-linked copolymer of the amine fluoride and acidic polymer on the tooth surface.

Optionally, the amine fluoride comprises hydroxyalkyl groups as the first reactive groups. Optionally, the hydroxyalkyl groups are hydroxyethyl groups.

Optionally, the amine fluoride comprises at least one $C_{10}$ to $C_{24}$ carbon chain. Optionally, the carbon chain has an even-numbered chain length. Optionally, the carbon chain is decyl, dodecyl (lauryl), tetradecyl (myristyl), hexadecyl (cetyl, palmityl), octadecyl (stearyl), eicosanyl, 9-cis-octadecen-1-yl (oleyl), 9-trans-octadecen-1-yl (elaidyl), cis,cis-9,12-octadecadien-1-yl (linolyl), cis,cis,cis-9,12,15-octadecatrien-1-yl (linolenyl) or 9-cis-eicosaen-1-yl (gadolyl). Optionally, the carbon chain is a $C_{18}$ carbon chain.

Optionally, the amine fluoride comprises at least one of Olaflur, Xidecaflur, and Steraflur.

Optionally, the amine fluoride is Olaflur and the tooth surface is also contacted with Dectaflur in step a). Optionally, the ratio of Olaflur to Dectaflur is from 20:1 to 1:1, optionally from 15:1 to 5:1, further optionally 10.6:1.

Optionally, the acidic polymer comprises carboxylic acid groups as the second reactive groups.

Optionally, the acidic polymer comprises monomers of maleic acid or maleic anhydride. Optionally, the acidic polymer is a copolymer of maleic acid or maleic anhydride with an alkylvinylether. Optionally, the alkylvinylether is methylvinylether.

Optionally, the acidic polymer comprises acrylic acid monomers. Optionally, the acidic polymer is polyacrylic acid.

Optionally, the concentration ratio of the amine fluoride to the acidic polymer in the oral care composition is from 1:1000 to 1:1; optionally from 1:100 to 1:2; optionally from 1:20 to 1:3.

Optionally, the tooth surface is also contacted with stannic oxide, $SnO_2$. Preferably, the stannic oxide is nano-particulate stannic oxide.

Optionally, the amine fluoride and the acidic polymer are maintained separately from one another prior to contacting with the tooth surface.

Optionally, the amine fluoride is present in a first oral care composition and the acidic polymer is present in a second oral care composition, the first and second oral care compositions being maintained separately from one another prior to contacting with the tooth surface. Optionally, the second composition is a mouthwash or a tooth gel.

Optionally, the amine fluoride is present in the first oral care composition in a concentration of 0.1 to 20 wt % based on the weight of the first oral care composition; optionally 1 to 15 wt % based on the weight of the first oral care composition; optionally 5 to 12 wt % based on the weight of the first oral care composition; optionally 9 wt % based on the weight of the first oral care composition.

Optionally, the acidic polymer is present in the second oral care composition in a concentration of 0.1 wt % to 30 wt %, based on the weight of the second oral care composition; optionally 1 wt % to 15 wt %, based on the weight of the second oral care composition; optionally 5 wt % to 12 wt %, based on the weight of the second oral care composition.

Optionally, stannic oxide is present in the first composition. Alternatively, stannic oxide may be present in the second composition. Preferably, the stannic oxide is nano-particulate stannic oxide:

A sixth aspect of the present invention provides an oral care composition of the present invention for use in the treatment or prevention of a disease or condition of the oral cavity.

Optionally, the disease or condition of the oral cavity is one or more of acid erosion, caries formation, demineralisation.

A seventh aspect of the present invention provides an oral care composition of the present invention for use in protection of a tooth surface against acid attack.

A eighth aspect of the present invention provides for use of an amine fluoride and an acidic polymer for forming a cross-linked polymer of the amine fluoride and acidic polymer on a tooth surface, wherein the amine fluoride and acidic polymer have respective first and second reactive groups which are arranged to react together to form a cross-linked copolymer of the amine fluoride and acidic polymer on a tooth surface.

Optionally, the amine fluoride comprises hydroxyalkyl groups as the first reactive groups. Optionally, the hydroxyalkyl groups are hydroxyethyl groups.

Optionally, the amine fluoride comprises at least one $C_{10}$ to $C_{24}$ carbon chain. Optionally, the carbon chain has an even-numbered chain length. Optionally, the carbon chain is decyl, dodecyl (lauryl), tetradecyl (myristyl), hexadecyl (cetyl, palmityl), octadecyl (stearyl), eicosanyl, 9-cis-octadecen-1-yl (oleyl), 9-trans-octadecen-1-yl (elaidyl), cis,cis-9,12-octadecadien-1-yl (linolyl), cis,cis,cis-9,12,15-octadecatrien-1-yl (linolenyl) or 9-cis-eicosaen-1-yl (gadolyl). Optionally, the carbon chain is a $C_{18}$ carbon chain.

Optionally, the amine fluoride comprises at least one of Olaflur, Xidecaflur, Steraflur and Oleaflur.

Optionally, the amine fluoride is Olaflur and the tooth surface is also contacted with Dectaflur. Optionally, the ratio of Olaflur to Dectaflur is from 20:1 to 1:1, optionally from 15:1 to 5:1, further optionally 10.6:1.

Optionally, the acidic polymer comprises carboxylic acid groups as the second reactive groups.

Optionally, the acidic polymer comprises monomers of maleic acid or maleic anhydride. Optionally, the acidic polymer is a copolymer of maleic acid or maleic anhydride with an alkylvinylether. Optionally, the alkylvinylether is methylvinylether.

Optionally, the acidic polymer comprises acrylic acid monomers. Optionally, the acidic polymer is polyacrylic acid.

Optionally, the concentration ratio of the amine fluoride to the acidic polymer is from 1:1000 to 1:1; optionally from 1:100 to 1:2; optionally from 1:20 to 1:3.

Optionally, the tooth surface is also contacted with stannic oxide, $SnO_2$. Preferably, the stannic oxide is nano-particulate stannic oxide.

Optionally, the amine fluoride and the acidic polymer are maintained separately from one another in the oral care composition prior to contacting with the tooth surface.

Optionally, the amine fluoride is present in a first oral care composition and the acidic polymer is present in a second oral care composition, the first and second oral care compositions being maintained separately from one another prior to contacting with the tooth surface. Optionally, the second composition is a mouthwash or a tooth gel.

Optionally, the amine fluoride is present in the first oral care composition in a concentration of 0.1 to 20 wt % based on the weight of the first oral care composition; optionally 1 to 15 wt % based on the weight of the first oral care composition; optionally 5 to 12 wt % based on the weight of the first oral care composition; optionally 9 wt % based on the weight of the first oral care composition.

Optionally, the acidic polymer is present in the second oral care composition in a concentration of 0.1 wt % to 30 wt %, based on the weight of the second oral care composition; optionally 1 wt % to 15 wt %, based on the weight of the second oral care composition; optionally 5 wt % to 12 wt %, based on the weight of the second oral care composition.

Optionally, the stannic oxide is present in the first composition. Alternatively, the oxide may be present in the second composition. Preferably, the stannic oxide is nano-particulate stannic oxide.

The compositions may also contain additional therapeutic and non-therapeutic components.

This invention is predicated on the finding by the present inventors that the formation on a tooth surface of a layer of cross-linked copolymer of an amine fluoride and an acidic polymer provides significant protection against acid attack.

DETAILED DESCRIPTION OF THE INVENTION

The following description of the preferred embodiment(s) is merely exemplary in nature and is in no way intended to limit the invention, its application, or uses.

The present invention provides an oral care composition comprising: (a) a first component comprising an amine fluoride; and (b) a second component comprising an acidic polymer; wherein the amine fluoride and acidic polymer have respective first and second reactive groups which are arranged to react together to form a cross-linked copolymer of the amine fluoride and acidic polymer when the composition is applied to an oral cavity.

The amine fluoride and the acidic polymer may be maintained separately from one another in the oral care composition. In one embodiment, the first component is a first oral care composition and the second component is a second oral care composition, and the first and second oral care compositions are maintained separately from one another. In certain embodiments, the second composition may be a mouthwash or a tooth gel.

In compositions of the present invention, the first component comprises an amine fluoride. The amine fluoride has reactive groups which are arranged to react with reactive groups of the acidic polymer to form a cross-linked copolymer of the amine fluoride and acidic polymer when the composition is applied to an oral cavity.

The amine fluoride may comprise hydroxyalkyl groups as the reactive groups. In particular, these hydroxyalkyl groups may be hydroxyethyl groups.

The amine fluoride may also comprise at least one $C_{10}$ to $C_{24}$ carbon chain of either even or odd-numbered chain length. Carbon chains having an even-numbered chain length may be preferred with regard to physiological acceptability. The carbon chain may be mono-unsaturated. Examples of saturated hydrocarbon residues having an even-numbered chain length are decyl, dodecyl (lauryl), tetradecyl (myristyl), hexadecyl (cetyl, palmityl), octadecyl (stearyl) and eicosanyl. Examples of unsaturated residues having an even-numbered chain length are 9-cis-octadecen-1-yl (oleyl), 9-trans-octadecen-1-yl (elaidyl), cis,cis-9,12-octadecadien-1-yl (linolyl), cis,cis,cis-9,12,15-octadecatrien-1-yl (linolenyl) or 9-cis-eicosaen-1-yl (gadolyl).

Examples of suitable amine fluorides include: Olaflur, Xidecaflur (also known as hydrofluoride of oleyldiethanolamine or Z-2,2'-(octadec-9-enylimino)bisethanol, CAS 13127-82-7), Steraflur (also known as hydrofluoride of stearyldiethanolamine, CAS 10213-78-2) and Oleaflur. A mixture of Olaflur and Dectaflur may also be used. When a mixture of Olaflur and Dectaflur is used, the ratio of Olaflur:Dectaflur may be from 20:1 to 1:1, optionally from 15:1 to 5:1, further optionally 10.6:1.

The amine fluoride may be present in the composition in a concentration of 0.1 wt % to 22 wt %, 1 wt % to 12 wt % or 6 wt % to 10 wt %, based on the total weight of the oral care composition.

In those embodiments where the oral care composition comprises a first oral care composition and a second oral care composition, the amine fluoride may be present in the first oral care composition in a concentration of 0.1 to 20 wt %, 1 to 15 wt %, 5 to 12 wt %, or 9 wt % based on the weight of the first oral care composition.

It is also envisaged that the amine fluoride could be made in situ, for example using an amine base and a fluoride-containing component (e.g. stannous fluoride) which can react to form an amine fluoride.

In compositions of the present invention, the second component comprises an acidic polymer. The acidic polymer has reactive groups which are arranged to react with the reactive groups of the amine fluoride to form a cross-linked copolymer of the amine fluoride and acidic polymer when the composition is applied to an oral cavity.

The acidic polymer may comprise carboxylic acid groups as the second reactive groups.

The acidic polymer may comprise monomers of maleic acid or maleic anhydride. The acidic polymer may be a copolymer of maleic acid or maleic anhydride with alkylvinylethers. The alkylvinylether may be methylvinylether. An example of a copolymer of maleic acid and methylvinylether is Gantrez S97 BF (sold by Ashland Speciality Ingredients).

The acidic polymer may comprise acrylic acid monomers. The acidic polymer may be polyacrylic acid.

The acidic polymer may be present in the oral care composition in a concentration of 0.1 wt % to 30 wt %, 1 wt % to 15 wt %, or 5 wt % to 12 wt %, based on the total weight of the oral care composition In those embodiments where the oral care composition comprises a first oral care composition and a second oral care composition, the acidic polymer may be present in the second oral care composition in a concentration of 0.1 wt % to 30 wt %, 1 wt % to 15 wt %, or 5 wt % to 12 wt %, based on the weight of the second oral care composition.

In certain embodiments, the concentration ratio of the amine fluoride to the acidic polymer in the oral care composition may be from 1:1000 to 1:1, from 1:100 to 1:2, or from 1:20 to 1:3.

The present inventors have surprisingly found that there is an unexpectedly fast interaction of the amine fluorides with acidic polymers to give a cross-linked copolymer of the amine fluoride and acidic polymer, without the need for any strong acid to catalyse the reaction. An example of such a reaction is between the amine fluoride Olaflur and the maleic acid/methylvinylether polymer Gantrez.

The present inventors have found that this reaction between Olaflur and Gantrez results in mixtures of insoluble esters of high molecular weight, as cross-linked polymers of the amine fluoride and the acidic polymer. These esters were found to be insoluble in water, ethanol and other organic solvents such as diethylether. The IR spectra of Olaflur alone; Gantrez alone; 1:1 Gantrez:Olaflur; 2:1 Gantrez:Olaflur; and 3:1 Gantrez:Olaflur were taken. The relative intensities of the new IR bands at 1562 cm$^{-1}$ and 1396 cm$^{-1}$ as seen in the spectra of the Gantrez/Olaflur mixtures are shown in Table 1, below:

TABLE 1

| Sample | 1633 cm$^{-1}$ | 1562 cm$^{-1}$ | 1479 cm$^{-1}$ | 1396 cm$^{-1}$ | 1229 cm$^{-1}$ | 1083 cm$^{-1}$ |
|---|---|---|---|---|---|---|
| 1 | ... | ... | 117 | ... | ... | ... |
| 2 | 147 | 210 | 208 | 181 | 136 | 223 |
| 3 | 162 | 194 | 198 | 168 | 136 | 209 |
| 4 | 147 | 194 | 188 | 162 | 123 | 200 |
| 5 | 194 | ... | ... | ... | 100 | 90 |

Sample 1: Olaflur 100%
Sample 2: Gantrez:Olaflur 1:1
Sample 3: Gantrez:Olaflur 2:1
Sample 4: Gantrez:Olaflur 3:1
Sample 5: Gantrez 100%

As can be seen from Table 1, the two bands at 1562 cm$^{-1}$ and 1396 cm$^{-1}$ are not visible in the spectra of either Gantrez alone or Olaflur alone. These bands are assigned to esterification products.

Esterification is usually controlled by equilibria with the simultaneous presence of the reaction products with the free acids and free alcohols, if the reaction products are all soluble in the solvent system. However, if the reaction products are insoluble in the solvent system, then the reaction products are removed from the system and the equilibrium is shifted towards the side of the reaction products i.e. the reaction becomes irreversible. The reaction hence completely proceeds from left to right:

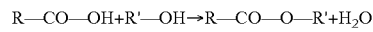

R—CO—OH+R'—OH→R—CO—O—R'+H$_2$O

The cross-linked polymers formed by the compositions of the present invention upon application to the oral cavity have been shown to provide significant protection properties against acid attack of the tooth surface (see Examples, below).

Applying such esterification products on surfaces such as tooth enamel, for example by first treatment with an amine fluoride-containing solution and then rinsing with a solution of an acidic polymer or brushing with a gel of the acidic polymer, would give in situ cross-linking to form an ester polymer of the acidic polymer and amine fluoride, which after drying has significant protection properties against any acid attack (see the Examples, below).

The present inventors have found that the pH range of the amine fluorides (pH of optionally 2.0 to 6.0, optionally 3.5 to 4.5) and the insolubility of the ester products (solubility of less than 100 ppm (w/w) in water) is sufficient for the formation of the cross-linked polymer.

It has been found that the protective effect of the compositions of the present invention can be improved by the addition of an inorganic additive. In particular, stannic oxide, SnO$_2$, may be added to the compositions of the present invention. Preferably, the stannic oxide is nanoparticulate stannic oxide.

In those embodiments where the oral care composition comprises a first oral care composition and a second oral care composition, the stannic oxide may be present in the first composition or in the second composition. In certain embodiments, the stannic oxide may be present in the oral care compositions in a concentration of 0.1 wt % to 3 wt %, 0.3 wt % to 2 wt %, or 0.5 wt % to 1 wt %, based on the total weight of the oral care composition. Preferably, the stannic oxide is nano-particulate stannic oxide.

Stannic oxide $SnO_2$ can be prepared by the very fast oxidation of stannous fluoride $SnF_2$ with singlet oxygen $^1O_2$, formed in situ with sodium hypochlorite and hydrogen peroxide:

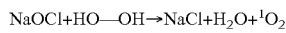

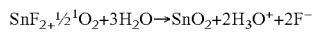

The formation of nano-particulate stannic oxide has been described in International patent application number PCT/EP2011/073831, which is incorporated herein by reference.

Together with the formation of the acid protective layer of the cross-linked copolymer of the amine fluoride and the acidic polymer, an additional incorporation of stannic oxide is believed to take place on the tooth enamel surface.

The oral care compositions according to the present invention may contain further additional therapeutic and non-therapeutic ingredients as known to those skilled in the art.

The compositions according to the invention comprise an orally acceptable vehicle. As used herein, an "orally acceptable vehicle" refers to a material or combination of materials that are safe for use in the compositions of the invention, commensurate with a reasonable benefit/risk ratio. Such materials include, for example, thickening agents, humectants, ionic active ingredients, buffering agents, anticalculus agents, abrasive polishing materials, peroxide sources, alkali metal bicarbonate salts, titanium dioxide, coloring agents, flavorings, sweetening agents, antimicrobial agents, herbal agents, desensitizing agents, stain reducing agents, and mixtures thereof. In those compositions where the oral care composition comprises a first oral care composition and a second oral care composition, such materials may be present in one or both of the first and second oral care compositions. The references to "the weight of the composition" as given below may be either the weight of the total oral care composition or, in those compositions where the oral care composition comprises a first oral care composition and a second oral care composition, to the weight of the first or second oral care composition in which the material is contained.

Surfactants may be included in the oral care compositions of the present invention to provide foaming, taste, flavor, texture and mouthfeel properties to the compositions, in particular to render the compositions more cosmetically acceptable. The surfactant components are each a detersive material that imparts to the composition detersive and foaming properties. Surfactants which may be included in the compositions of the present invention include anionic, cationic, zwitterionic, amphoteric or non-ionic surfactants.

The compositions of the present invention may also include a water-phase containing at least one humectant. The humectant concentration typically totals about 5 to about 75% by weight of the composition, optionally from 35 to 75 wt % based on the weight of the composition, further optionally from 45 to 65 wt % based on the weight of the composition. The at least one humectant may comprise a mixture of sorbitol, glycerin and xylitol, typically in a concentration of from 25 to 45 wt % sorbitol, from 5 to 15 wt % glycerin and from 5 to 15 wt % xylitol, each amount being based on the weight of the composition. Reference herein to sorbitol refers to the material typically commercially available as a 70 wt % aqueous solution. In other words, when the orally acceptable vehicle comprises from 25 to 45 wt % sorbitol, this means the active sorbitol concentration is from 17.5 to 31.5 wt %, each amount being based on the weight of the composition.

The humectant is optionally glycerin, sorbitol, xylitol, and/or propylene glycol of molecular weight in the range of 200 to 1,000; but, other humectants and mixtures thereof may also be employed.

Water is present typically in amount of at least about 10 wt %, and generally about 25 to 70 wt % of the composition. Water employed in the preparation of commercially suitable oral care compositions may be deionized and free of organic impurities. These amounts of water include the free water which is added plus that which is introduced with other materials such as with sorbitol.

Flavoring agents that may be used in the compositions of the present invention include essential oils as well as various flavoring aldehydes, esters, alcohols, and similar materials. Examples of the essential oils include oils of spearmint, peppermint, aniseed, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint. The flavoring agent may be incorporated in the oral care composition at a concentration of 0.1 to 5 wt % and typically 0.5 to 1.5 wt %. In those embodiments where the oral care composition comprises a first oral care composition and a second oral care composition and the second oral care composition is a mouthwash, these flavourings may be present in the second oral care composition in an amount of 0 wt % to 0.5 wt %, optionally 0.03 wt % to 0.3 wt % based on the weight of the second oral care composition. In those embodiments where the oral care composition comprises a first oral care composition and a second oral care composition and the second oral care composition is a tooth gel, these flavourings may be present in the second oral care composition in an amount of 0.1 to 5 wt %, optionally 0.5 to 1.5 wt % based on the weight of the second oral care composition.

Sweetening agents which may be used in the compositions of the present invention include artificial sweeteners such as saccharin, acesulfam, neotam, cyclamate or sucralose; natural high-intensity sweeteners such as thaumatin, stevioside or glycyrrhizin; or sugar alcohols such as sorbitol, xylitol, maltitol or mannitol. These may be present in amounts of 0 wt % to 0.2 wt %, optionally 0.005 wt % to 0.1 wt % based on the weight of the composition.

Antibacterials and/or preservatives, such as chlorhexidine, triclosan, quaternary ammonium compounds (such as benzalkonium chloride) or parabens (such as methyl or propyl paraben) may be used in the compositions. The amount of antimicrobial agent is typically from 0 to about 0.5 wt %, optionally 0.05 to 0.1 wt % based on the weight of the composition.

Emulsifiers or solubilisers may also be used, mainly in connection with abovementioned flavourings and/or antibacterials, which often are of low solubility in aqueous media. Examples of such emulsifiers are neutral surfactants (such as polyoxyethylene hydrogenated castor oil or fatty acids of sugars), anionic surfactants (such as sodium lauryl sulphate), cationic surfactants (such as the ammonium cations of formula (I)) or zwitterionic surfactants. These surfactants or solubilisers may be present in amounts of typically 0 wt % to 2 wt %, optionally 0.2 wt % to 1.5 wt % based on the weight of the composition.

Thickeners suitable for use in the compositions of the present invention include natural and synthetic gums and colloids. Suitable thickeners include naturally occurring polymers such as carrageenan, xanthan gum, polyglycols of varying molecular weights sold under the tradename Polyox, and polyvinylpyrrolidone. Compatible inorganic thickeners include amorphous silica compounds which function as thickening agents and include colloidal silicas compounds available under the trade designation Cab-o-sil manufactured by Cabot Corporation and distributed by Lenape Chemical, Bound Brook, N.J.; Zeodent 165 from J. M. Huber Chemicals Division, Havre de Grace, Md. 21078; and Sylodent 15, available from Davison Chemical Division of W. R. Grace Corporation, Baltimore, Md. 21203. Other inorganic thickeners include natural and synthetic clays such as hectorite clays, lithium magnesium silicate (laponite) and magnesium aluminum silicate (Veegum).

The thickening agent optionally is present in the composition in amounts of 0.1 to 10 wt %, optionally 3 to 7 wt % based on the weight of the composition.

The oral care compositions of the present invention may also include antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$ sodium tripolyphosphate, long chain polyphosphates such as sodium hexametaphosphate and cyclic phosphates such as sodium trimetaphosphate.

The compositions of the present invention may also include an abrasive.

Abrasives that may be used include silica abrasives such as precipitated or hydrated silicas having a mean particle size of up to about 20 microns, such as Zeodent 105 and Zeodent 114 marketed by J.M. Huber Chemicals Division, Havre de Grace, Md. 21078, or Sylodent 783 marketed by Davison Chemical Division of W.R. Grace & Company. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

Possible abrasive materials include silica gels and precipitated amorphous silica having an oil absorption value of less than 100 cc/100 g silica and optionally in the range of from about 45 cc/100 g to less than about 70 cc/100 g silica. These silicas are colloidal particles having an average particle size ranging from about 3 microns to about 12 microns, and optionally between about 5 to about 10 microns and a pH range from 4 to 10 optionally 6 to 9 when measured as a 5% by weight slurry.

The abrasive may be present in an amount of from 15 to 35 wt % based on the weight of the composition, optionally from 20 to 30 wt % based on the weight of the composition.

The compositions according to the invention may be administered to or applied to a human or other animal subject. The compositions are suitable for administration or application to the oral cavity of a human or animal subject.

The present invention also provides methods of protecting a tooth surface against acid attack, and methods of treating or preventing a disease or condition of the oral cavity, comprising applying an oral care composition of the present invention to the oral cavity or tooth surface.

In one embodiment, the present invention provides a method of treating or preventing a disease or condition of the oral cavity, comprising applying an oral care composition according to the present invention to the oral cavity.

In another embodiment, the present invention provides a method of protecting a tooth surface against acid attack, comprising applying an oral care composition according to the present invention to the tooth surface.

The present invention also provides a method of treating or preventing a disease or condition of the oral cavity, comprising the steps of: (a) contacting an oral surface with an amine fluoride; and subsequently (b) contacting the oral surface with an acidic polymer; wherein the amine fluoride and acidic polymer have respective first and second reactive groups which are arranged to react together to form a cross-linked copolymer of the amine fluoride and acidic polymer on the oral surface.

The present invention also provides a method of protecting a tooth surface against acid attack, comprising the steps of: (a) contacting the tooth surface with an amine fluoride; and subsequently (b) contacting the tooth surface with an acidic polymer; wherein the amine fluoride and acidic polymer have respective first and second reactive groups which are arranged to react together to form a cross-linked copolymer of the amine fluoride and acidic polymer on the tooth surface.

Various embodiments now will be described with reference to the following non-limiting examples.

EXAMPLE 1

A calcium carbonate plate was divided into two halves (a left-hand side and a right-hand side). Drops of an amine fluoride solution (9% Olaflur from Elmex® fluid with 1% $F^-$) were added to various locations on the left-hand side of the plate, followed by subsequent application of Gantrez S97 to these same locations. The amine fluoride and Gantrez immediately formed a cross-linked ester polymer film on the surface of the calcium carbonate plate. The right-hand side of the plate was not treated with either amine fluoride or Gantrez.

After allowing the treated locations of the plate to dry, drops of 0.1N aqueous hydrochloric acid (HCl, pH 1) were applied to the treated locations on the left hand side of the plate, and were also applied to various locations on the untreated right-hand side of the plate. In order to show a change in the pH value on the plate, the indicator Alizarin Red was added to the aqueous hydrochloric acid.

The areas on the left-hand side which were treated with amine fluoride solution and Gantrez show no acid attack i.e., the pH value of the acid remains at about pH 1 thus indicating that the acid has not reacted with the calcium carbonate (which is protected by the amine fluoride/Gantrez). However, on the untreated right-hand side of the plate, there is evidence of acid attack i.e., the pH has changed from pH 1 to pH 6-7 due to reaction of the acid with the calcium carbonate.

EXAMPLE 2

A similar test was carried out using three products: Olaflur (as Elmex® fluid) alone; the cross-linking reaction product of Olaflur (as Elmex® fluid) and Gantrez; and Gantrez alone. In principle, all three of these products should be able to protect the acid-sensitive calcium carbonate plate from attack by hydrochloric acid.

The spots on the calcium carbonate plate (two hours after the addition of the acid) are as follows:

TABLE 3

| | Treatment | Colour of spots |
|---|---|---|
| | Left-hand side: | |
| Top | elmex® fluid (2 drops) & 0.1N HCl (1 drop) | violet |
| Middle | elmex® fluid (2 drops) & Gantrez S97 (4 drops) & 0.1N HCl (1 drop) | yellow |
| Bottom | Gantrez S97 (4 drops) & 0.1N HCl (1 drop) | orange |
| | Right-hand side: | |
| Top | unprotected calcium carbonate surface & 0.1N HCl (1 drop) | violet |
| Middle | unprotected calcium carbonate surface & 0.1N HCl (1 drop) | violet |
| Bottom | unprotected calcium carbonate surface & 0.1N HCl (1 drop) | violet |

During the first minutes after the application of the drops of 0.1N hydrochloric acid, each of the spots on the left hand side of the plate were yellow in colour. However, after two hours drying time the spot treated with Elmex® fluid (top left hand side) showed the violet colour corresponding to neutralisation of the acid by reaction with the calcium carbonate layer. This is observed due to the aqueous hydrochloric acid diluting and partially dissolving the amine fluoride layer on the plate, thus allowing the acid to react with the underlying calcium carbonate.

After 2 hours drying time, the Elmex® fluid/Gantrez spot (middle left hand side) shows a clear superiority in protection of the calcium carbonate against acid attack, as compared to Elmex® fluid alone (top left hand side) and Gantrez (bottom left hand side) alone. The best protecting effect was seen with the cross-linking product of amine fluoride and Gantrez, followed then by Gantrez alone and finally by Elmex® fluid alone.

The plate was then rigorously rinsed with water and, on the same spots, a second acid attack was applied. The results of the spots on the calcium carbonate plate are as follows:

TABLE 4

| Left hand side | Treatment | Colour |
|---|---|---|
| Top | As Table 3, left hand side, with additional acid | Red/orange |
| Middle | As Table 3, left hand side, with additional acid | Yellow/orange |
| Bottom | As Table 3, left hand side, with additional acid | Red/orange |

As can be seen from the still yellow-ish coloured spot on the middle left-hand side of the plate, there is still significant protection provided to the calcium carbonate surface by the cross-linked polymer of amine fluoride and Gantrez against a second acid attack.

Even after a further washing process and a third acid attack, the spot of amine fluoride/Gantrez still appeared to provide greater protection of the calcium carbonate plate than the amine fluoride alone or the Gantrez alone, in which the spots on the calcium carbonate plate are as follows:

TABLE 5

| Left hand side | Treatment | Colour |
|---|---|---|
| Top | As Table 4, left hand side, with additional acid | Red/orange |
| Middle | As Table 4, left hand side, with additional acid | Yellow/orange |
| Bottom | As Table 4, left hand side, with additional acid | Red/orange |

The increased protection provided by the spot of amine fluoride/Gantrez was also evident even after abrading and polishing the surface of the calcium carbonate plate. The spot of the amine fluoride/Gantrez polymer is no longer visible following abrasion, and there are only very slight traces of erosion and only a very small acid-etching depth which is significantly lower than for the spots of both amine fluoride alone and Gantrez alone, or for the spots on the unprotected right hand side of the plate. In addition, the polished surface of the amine fluoride/Gantrez spot showed a significantly smoother surface structure than the other spots.

The protection of the calcium carbonate layer against acid attack by (respectively) Olaflur alone and by an Olaflur/Gantrez cross-linked copolymer is seen where the aqueous hydrochloric acid penetrates the non-protected surface of the calcium carbonate, with formation of calcium chloride and carbon dioxide. The Olaflur (as Elmex® fluid) is able to protect the calcium carbonate surface. However, after some hours, the layer of water-soluble amine fluoride is diluted and dissolved by the attacking aqueous acid. However, an optimal protection of the acid sensitive surface (e.g. calcium carbonate, hydroxyapatite or tooth enamel) can be achieved by the cross-linked copolymer of amine fluoride and Gantrez. The protection is present for at least several hours, possibly even days.

It is believed that the first contact of the calcium carbonate surface with fluoride ions from the amine fluoride results in the formation of a layer of $CaF_2$ with a Mohs hardness of 4 (calcium carbonate having a Mohs hardness of 3). This $CaF_2$ layer is then thought to be additionally protected by the amine fluoride/Gantrez cross-linked polymer.

EXAMPLE 3

It has also been found that the cross-linking of the acidic polymer with the amine fluoride takes place at concentrations of acidic polymer as little as 0.1 wt % (and even lower), and concentrations of amine fluoride as little as 0.1 wt. %.

Gantrez S97 BF was diluted with water to a concentration of 0.1 wt. % to form an aqueous solution containing 0.1 wt. % GantrezAn aqueous solution of 20 wt. % Olaflur in water (corresponding to 1.4 wt. % fluoride) was also diluted so as to provide an aqueous solution containing 0.1 wt. % Olaflur.

The following amounts of the above 0.1 wt. % Gantrez solution and the 0.1 wt. % Olaflur solution were mixed together:

EXPERIMENT 1

10 g of the 0.1 wt. % Gantrez solution was mixed with 1.78 g of the 0.1 wt. % Olaflur solution. The mixture was observed to be very turbid, which turbidity was attributed to the formation of insoluble esters in the cross-linking reaction of Gantrez and Olaflur. The concentration of Gantrez in the mixture was [10/(10+1.78)]*0.1=0.084 wt. % (i.e. approximately 0.1 wt. %).

EXPERIMENT 2

1.36 g of the 0.1 wt. % Gantrez solution was mixed with 1.78 g of the 0.1 wt. % Olaflur solution. The mixture was observed to be turbid, which turbidity was attributed to the formation of insoluble esters in the cross-linking reaction of Gantrez and Olaflur. The concentration of Gantrez in the mixture was [1.36/(136+1.78)]*0.1=0.043 wt. % (i.e. approximately 0.04 wt. %).

EXPERIMENT 3

0.13 g of the 0.1 wt. % Gantrez solution was mixed with 1.78 g of the 0.1 wt. % Olaflur solution. The mixture was observed to be turbid, which turbidity was attributed to the formation of insoluble esters in the cross-linking reaction of Gantrez and Olaflur. The concentration of Gantrez in the mixture was [0.13/(0.13+1.78)]*0.1=0.0068 wt. % (i.e. approximately 0.007 wt. %).

EXPERIMENT 4

0.06 g of the 0.1 wt. % Gantrez solution was mixed with 1.78 g of the 0.1 wt. % Olaflur solution. The mixture was observed to be slightly turbid, which turbidity was attributed to some formation of insoluble esters in the cross-linking reaction of Gantrez and Olaflur. The concentration of Gantrez in the mixture was [0.06/(0.06+1.78)]*0.1=0.0033 wt. % (i.e. approximately 0.003 wt. %).

EXPERIMENT 5

0.03 g of the 0.1 wt. % Gantrez solution was mixed with 1.87 g of the 0.1 wt. % Olaflur solution. The mixture was observed to be slightly turbid, which turbidity was attributed to some formation of insoluble esters in the cross-linking reaction of Gantrez and Olaflur. The concentration of Gantrez in the mixture was [0.03/(0.03+1.87)]*0.1=0.0016 wt. % (i.e. approximately 0.002 wt. %).

EXPERIMENT 6

0.0491 g of the 0.1 wt. % Gantrez solution was mixed with 1.77 g of the 0.1 wt. % Olaflur solution. The mixture was observed to be slightly turbid, which turbidity was attributed to some formation of insoluble esters in the cross-linking reaction of Gantrez and Olaflur. The concentration of Gantrez in the mixture was [0.0491/(0.0491+1.77)]*0.1=0.00270 wt. % (i.e. approximately 0.003 wt. %).

10 drops of each of the six turbid liquid mixtures of Experiments 1 to 6 (above) were dropped on to a glass plate, dried using a heating plate, and then covered with a second glass plate. The insoluble ester cross-linking products of the reaction between Gantrez and Olaflur were then viewed on a suitable light-reflecting background (in this case, aluminium foil) using an optical scanner, e.g., an HP Color Laser Jet CM 4730 MFP. The results are as follows:

EXPERIMENT 1

Appearance on Glass Plate

As detailed above, 10 g of 0.1 wt. % Gantrez solution and 1.78 g of 0.1 wt. % Olaflur solution were mixed together in Experiment 1 (concentration level of Gantrez in mixture=0.084 wt. %). On the glass surface, the layer of cross-linked ester product showed a very fine structure, i.e., a thin layer-film of the reaction-mixture which could not be directly visualised using the optical scanner, but was nevertheless clearly observable by the naked eye. On the glass plate, the very fine structure can be seen by the formation of some small, thin lines of the cross-linked product, e.g., somewhat comparable to contours on a map, which indicates the cross-linked product, which is deposited on the glass-surface, e.g., with some clear boundaries, but only visible by eye and not on the printed picture after scanning. It is further hypothesised that the cross-linked ester product might be strongly adsorbed on the glass surface (for example to a greater extent than Olaflur alone).

EXPERIMENT 2

Appearance on Glass Plate

As detailed above, 1.36 g of 0.1 wt. % Gantrez solution and 1.78 g of 0.1 wt. % Olaflur solution were mixed together in Experiment 2 (concentration level of Gantrez in mixture=0.043 wt. %). The layer of cross-linked ester product again showed a very fine structure on the glass plate which were attributable to the cross-linking product, but different lines appeared which were attributed to the excess amount of Olaflur present.

EXPERIMENT 3

Appearance on Glass Plate

As detailed above, 0.13 g of 0.1 wt. % Gantrez solution and 1.78 g of 0.1 wt. % Olaflur solution were mixed together in Experiment 3 (concentration level of Gantrez in mixture=0.0068 wt. %). The layer of cross-linked ester product again showed a fine structure on the glass plate, but the Olaflur layer was more predominate.

EXPERIMENT 4

Appearance on Glass Plate

As detailed above, 0.06 g of 0.1 wt. % Gantrez solution and 1.78 g of 0.1 wt. % Olaflur solution were mixed together in Experiment 4 (concentration level of Gantrez in mixture=0.0033 wt. %). The fine structure of the cross-linked ester product layer was still partially seen on the glass plate, but the Olaflur layer was more predominate.

EXPERIMENT 5

Appearance on Glass Plate

As detailed above, 0.03 g of 0.1 wt. % Gantrez solution and 1.87 g of 0.1 wt. % Olaflur solution were mixed together in Experiment 5 (concentration level of Gantrez in mixture=0.0016 wt. %). The fine structure of the cross-linked ester product layer was still partially seen on the glass plate, but the Olaflur layer was more predominate.

EXPERIMENT 6

Appearance on Glass Plate

As detailed above, 0.0491 g of 0.1 wt. % Gantrez solution and 1.77 g of 0.1 wt. % Olaflur solution were mixed together in Experiment 6 (concentration level of Gantrez in mixture=0.00270 wt. %). The fine structure of the cross-linked ester product layer was still partially seen on the glass plate, but the Olaflur layer was more predominate.

It can be seen from the above results that the cross-linking reaction between the acidic polymer Gantrez and the amine fluoride Olaflur takes place at a concentration of as little as 0.1 wt. % Gantrez. It can also be seen that a concentration of 0.04 wt. % Gantrez in the mixture would still result in cross-linking with the Olaflur, and that cross-linking products are also formed to some extent when the concentration of Gantrez in the mixture is as little as about 0.04 wt. % or 0.01 wt. %. Lower concentrations of Gantrez (e.g. 0.003 wt. %) in the mixture may also result in the formation of cross-linked ester products with Olaflur; however (without wishing to be bound by any theory) it is believed that the insoluble ester products are present in very small amounts in such mixtures in the presence of an excess of Olaflur:

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

We claim:

1. An oral care composition, comprising:
(a) a first component comprising an amine fluoride; and
(b) a second component comprising an acidic polymer;
wherein the amine fluoride and acidic polymer have respective first and second reactive groups which are arranged to react together to form a cross-linked copolymer of the amine fluoride and acidic polymer when the composition is applied to an oral cavity, and wherein the amine fluoride and the acidic polymer are maintained separately from one another in the oral care composition prior to contacting with the oral surface; wherein the amine fluoride is N,N,N'-tris(2-hydroxyethyl)-N'-octadecylpropane-1,3-diamine dihydrofluoride and wherein the acidic polymer is a copolymer of maleic acid or maleic anhydride with methyl vinyl ether.

2. The oral care composition of claim 1, wherein the amine fluoride is present in a concentration of 0.1 wt % to 22 wt %, based on the total weight of the oral care composition.

3. The oral care composition of claim 1, wherein the acidic polymer is present in a concentration of 0.1 wt % to 30 wt %, based on the total weight of the oral care composition.

4. The oral care composition of claim 1, wherein the concentration ratio of the amine fluoride to the acidic polymer in the oral care composition is from 1:1000 to 1:1.

5. The oral care composition of any preceding claim 1, further comprising stannic oxide, $SnO_2$.

6. The oral care composition of claim 5, wherein the stannic oxide is present in the oral care composition in a concentration of 0.1 wt % to 3 wt %, based on the total weight of the oral care composition.

7. The oral care composition of claim 1, wherein the anime fluoride is present in a concentration of 0.1 to 20 wt % based on the weight of the first oral care composition.

8. The oral care composition of claim 1, wherein the acid polymer is present in the second oral care composition in a concentration of 0.1 wt % to 30 wt %, based on the weight of the second oral care composition.

9. The oral care composition of claim 1, further comprising stannic oxide in the first composition.

10. The oral care composition of claim 1, further comprising stannic oxide in the first composition.

11. A method of treating or preventing a disease or condition of the oral cavity, comprising applying an oral care composition according to claim 1 to the oral cavity.

12. The method of claim 11, wherein the disease or condition of the oral cavity is one or more of acid erosion, caries formation, demineralisation.

13. A method of protecting a tooth surface against acid attack, the method comprising applying an oral care composition according to claim 1 to the tooth surface.

14. A method of treating or preventing a disease or condition of the oral cavity, comprising the steps of:
(a) contacting an oral surface with a first component, of an oral care composition, comprising an amine fluoride; and subsequently
(b) contacting the oral surface with a second component, of an oral care composition, comprising an acidic polymer;
wherein the film-forming amine fluoride and film-forming acidic polymer have respective first and second reactive groups which are arranged to react together to form a cross-linked copolymer of the amine fluoride and acidic polymer on the oral surface, wherein the cross-linked copolymer is a film-former, and wherein the amine fluoride and the acidic polymer are maintained separately from one another prior to contacting with the oral surface; wherein the amine fluoride comprises hydroxyalkyl groups as the first reactive groups; wherein amine fluoride is N,N,N'-tris(2-hydroxyethyl)-N'-octadecylpropane-1,3-diamine dihydrofluoride, and wherein the acidic polymer is a copolymer of maleic acid or maleic anhydride with methyl vinyl ether.

15. The method of claim 14, wherein the disease or condition of the oral cavity is one or more of caries formation, acid erosion, demineralization.

16. The method of claim 14, wherein the concentration ratio of the amine fluoride to the acidic polymer is from 1:1000 to 1:1.

17. The method of claim 14, wherein the oral surface is also contacted with stannic oxide, $SnO_2$.

18. The method of claim 14, wherein the amine fluoride is present in a concentration of 0.1 to 20 wt % based on the weight of the first oral care composition.

19. The method of claim 14, wherein the acidic polymer is present in the second oral care composition in a concentration of 0.1 wt % to 30 wt %, based on the weight of the second oral care composition.

20. The method of claim 14, further comprising stannic oxide in the first composition.

21. The method of claim 14, further comprising stannic oxide in the second composition.

22. A method of protecting a tooth surface against acid attack, comprising the steps of:
(a) contacting the tooth surface with a first component, of an oral care composition, comprising an amine fluoride; and subsequently
(b) contacting the tooth surface with a second component, of an oral care composition, comprising an acidic polymer;
wherein the film-forming amine fluoride and film-forming acidic polymer have respective first and second reactive groups which are arranged to react together to form a cross-linked copolymer of the amine fluoride and acidic polymer on the tooth surface, wherein the cross-linked copolymer is a film-former, and wherein the amine fluoride and the acidic polymer are maintained separately from one another prior to contacting with the tooth surface; wherein the amine fluoride comprises hydroxyalkyl groups as the first reactive groups; wherein amine fluoride is N,N,N'-tris(2-hydroxyethyl)-N'-octadecylpropane-1,3-diamine dihydrofluoride and wherein the acidic polymer is a copolymer of maleic acid or maleic anhydride with methyl vinyl ether.

23. The method of claim 22, wherein the concentration ratio of the amine fluoride to the acidic polymer is from 1:1000 to 1:1.

24. The method of claim 22, wherein the tooth surface is also contacted with stannic oxide, $SnO_2$.

25. The method of claim 22, wherein the amine fluoride is present in a first oral care composition and the acidic polymer is present in a second oral care composition, the first and second oral care compositions being maintained separately from one another prior to contacting with the tooth surface.

26. The method of claim 25, wherein the amine fluoride is present in a concentration of 0.1 to 20 wt % based on the weight of the first oral care composition.

27. The method of claim 25 wherein the acidic polymer is present in the second oral care composition in a concentration of 0.1 wt % to 30 wt %, based on the weight of the second oral care composition.

28. The method of claim 25, further comprising stannic oxide in the first composition.

29. The method of claim 25, further comprising stannic oxide in the second composition.

* * * * *